(12) United States Patent
Hutchings et al.

(10) Patent No.: US 9,108,896 B2
(45) Date of Patent: Aug. 18, 2015

(54) METHOD OF MAKING ALCOHOLS

(75) Inventors: Graham John Hutchings, Hereford and Worcester (GB); Muhammad Hasnain Haider, South Glamorgan (GB); Nicholas Francois Dummer, South Glamorgan (GB); Stuart Hamilton Taylor, South Glamorgan (GB); David William Knight, Vale of Glamorgan (GB)

(73) Assignee: UNIVERSITY COLLEGE CARDIFF CONSULTANTS LIMITED, Cardiff, South Glamorgan (GB)

( * ) Notice: Subject to any disclaimer, the term of this patent is extended or adjusted under 35 U.S.C. 154(b) by 0 days.

(21) Appl. No.: 14/237,310

(22) PCT Filed: Aug. 9, 2012

(86) PCT No.: PCT/GB2012/051931
§ 371 (c)(1),
(2), (4) Date: Jun. 17, 2014

(87) PCT Pub. No.: WO2013/024261
PCT Pub. Date: Feb. 21, 2013

(65) Prior Publication Data
US 2014/0323774 A1    Oct. 30, 2014

(51) Int. Cl.
| C07C 29/60 | (2006.01) |
| C07C 29/00 | (2006.01) |
| B01J 37/03 | (2006.01) |
| B01J 37/04 | (2006.01) |
| B01J 37/08 | (2006.01) |
| B01J 21/10 | (2006.01) |
| B01J 23/02 | (2006.01) |
| B01J 23/10 | (2006.01) |
| B01J 35/02 | (2006.01) |
| B01J 35/10 | (2006.01) |

(52) U.S. Cl.
CPC ............... *C07C 29/60* (2013.01); *B01J 21/10* (2013.01); *B01J 23/02* (2013.01); *B01J 23/10* (2013.01); *B01J 35/023* (2013.01); *B01J 35/1009* (2013.01); *B01J 35/1019* (2013.01); *B01J 37/036* (2013.01); *B01J 37/04* (2013.01); *B01J 37/08* (2013.01); *C07C 29/00* (2013.01); *C07B 2200/05* (2013.01)

(58) Field of Classification Search
None
See application file for complete search history.

(56) References Cited

U.S. PATENT DOCUMENTS

| 7,259,280 B1 | 8/2007 | Kahn et al. |
| 2007/0225383 A1 | 9/2007 | Cortright et al. |
| 2010/0022807 A1 | 1/2010 | D'Hondt et al. |

FOREIGN PATENT DOCUMENTS

| CN | 101759529 | 6/2010 |
| DE | 102008031828 | 1/2010 |
| JP | 2006-212496 | 8/2006 |
| JP | 2009-275029 | 11/2009 |
| WO | WO 81/03181 | 11/1981 |
| WO | WO 2009/130452 | 10/2009 |
| WO | WO 2011/045605 | 4/2011 |

OTHER PUBLICATIONS

International Search Report and Extract from preamble of International Patent Application PCT/GB2012/051931, Nov. 20, 2012.
UK Search Report GB1113904.5, Nov. 23, 2011.
Extract from Wikipedia for "Methanol", Jun. 30, 2011 (9 pages).
M. Calatayud: "Ethylene glycol interaction on alkaline earth oxides"; Catalysis Today, vol. 152, 2010, pp. 88-92.
X. Guo et al.: "Co/MgO catalysts for hydrogenolysis of glycerol to 1,2-propanediol"; Applied Catalysis A: General, vol. 371, No. 1-2, 2009, pp. 108-113.

*Primary Examiner* — Yong Chu
*Assistant Examiner* — Ana Z Muresan
(74) *Attorney, Agent, or Firm* — Hamre, Schumann, Mueller & Larson, P.C.

(57) ABSTRACT

A method of making one or more alcohols with a single hydroxy group, such as methanol and ethanol, the method comprising contacting a polyol and water with a basic catalyst. The polyol may be glycerol, for example. The catalyst may be magnesium oxide.

19 Claims, No Drawings

METHOD OF MAKING ALCOHOLS

The present invention relates to a method of making one or more alcohols, in particular alcohols with a single hydroxy group, such as methanol and/or ethanol.

BACKGROUND

Methanol and ethanol are useful industrial chemicals which may be used to make, inter alia, biodiesel. Ethanol is typically made commercially by the hydration of ethylene or the fermentation of starch. The ethylene is often obtained by steam cracking fossil fuels. Methanol is typically made by reacting carbon monoxide and hydrogen in the presence of a catalyst (the carbon monoxide and hydrogen often being generated in the synthesis of methane). There are problems with the methods described above. The synthesis of methane and hydration of ethylene rely on fossil fuel products, which may in the future become scarce and/or expensive. The fermentation of starch to produce ethanol can be expensive, depending on the price of the source of the starch (typically cassava).

There have been attempts to make ethanol and/or methanol from waste materials or by-products. One such waste material or by-product is glycerol. Glycerol is a by-product of the production of biodiesel and of the processing of vegetable oils. WO2009/130452 describes a method of making methanol in which a sugar alcohol (such as glycerol) is treated with high pressure hydrogen in the presence of a transition metal hydrogenolysis catalyst. The use of high pressure hydrogen gas may be undesirable, however, because hydrogen gas is explosive and the use of high pressures requires the use of containers which can withstand the pressures used.

BRIEF SUMMARY

The method of the present invention seeks to ameliorate one or more of the problems mentioned above.

There is provided in accordance with the present invention, a method of making one or more alcohols with a single hydroxy group, the method comprising contacting a polyol with a basic catalyst.

DETAILED DESCRIPTION

The applicant has unexpectedly discovered that it is possible to treat polyols so as to form one or more alcohols with a single hydroxy group (such as ethanol and methanol) without the use of hydrogen gas.

Therefore, the method typically comprises contacting the polyol with a basic catalyst in the absence of a flow of hydrogen gas.

The polyol is preferably in the gas phase when contacted with the catalyst.

For the avoidance of doubt, the phrase "with a single hydroxy group" means that the alcohol contains one (and only one) —OH group.

The method is preferably is method of making one or both of methanol and ethanol. This may typically be achieved using a polyol such as ethylene glycol or glycerol, for example.

Without wishing to be bound by theory, it is believed that the polyol may act as a hydrogen donor.

The method may comprise contacting the polyol with a basic catalyst in the presence of water. Without wishing to be bound by theory, it is believed that the water is acting as a hydrogen donor.

The polyol may typically be mixed with the water.

If the polyol is contacted with a basic catalyst in the presence of water, or if the polyol is mixed with water, the weight of the water may optionally be greater than the weight of the polyol.

If the polyol is contacted with a basic catalyst in the presence of water, or if the polyol is mixed with water the weight of polyol may be from 0.001 to 10 times the weight of the water, optionally from 0.001 to 2 times the weight of the water, optionally from 0.001 to 0.5 times the weight of the water, optionally from 0.003 to 0.1 times the weight of the water, and optionally from 0.1 to 0.5 times the weight of the water.

The term "polyol" indicates that a compound has two or more hydroxy (—OH) groups.

The polyol may comprise a polyhydroxyalkane, such as propane-1,2-diol, propane-1,3-diol, propane-1,2,3-triol (glycerol) or butane-1,4-diol. The term "polyol" also includes sugars, such as glucose, lactose and galactose, typically monosaccharide or disaccharide sugars, especially monosaccharide sugars. The method of the present invention has been found to be particularly effective in making methanol from glycerol.

The polyol may optionally contain up to 6 carbon atoms, and may typically contain 2, 3, 4 or 6 carbon atoms, and preferably 2 or 3 carbon atoms. The polyol may typically comprise up to 6 hydroxy groups, and may optionally comprise 2, 3 or 4 hydroxy groups. Optionally, hydroxy groups may be provided on adjacent carbon atoms. Typically, no carbon atom is provided with more than one hydroxy group.

The ambient pressure when the polyol is typically contacted with the catalyst is typically 5 atmospheres or less, optionally 3 atmospheres or less, optionally 2 atmospheres or less and optionally from 1.0 to 1.5 atmospheres.

The catalyst may comprise one or more metals, typically one or more alkaline earth metals (i.e. one or more of beryllium, magnesium, calcium, strontium, barium and radium) and/or one or more lanthanide (such as lanthanum). The catalyst preferably comprises one or more of magnesium, calcium, strontium, barium, lanthanum, praseodymium, neodymium, promethium, samarium, europium, gadolinium, terbium, dysprosium, holmium, erbium, thulium, ytterbium and lutetium. The catalyst may comprise one or more metal oxides. The catalyst may comprise one or more oxides of one or more alkaline earth metal. The catalyst may comprise one or more of magnesium oxide, calcium oxide, strontium oxide, barium oxide and lanthanum oxide. The catalyst may comprise one or more oxides of one or more lanthanide. The catalyst may comprise one or more alkaline earth metal or one or more lanthanide, and a further (non-alkaline earth and non-lanthanide) metal. For example, the catalyst may further comprise lithium. The catalyst may further comprise manganese.

The catalyst may comprise magnesium oxide and calcium oxide. The catalyst may comprise from 10 wt % to 90 wt % magnesium oxide and from 10 wt % to 90 wt % calcium oxide. The catalyst may comprise from 25 wt % to 75 wt % magnesium oxide, and may comprise from 25 wt % to 75 wt % calcium oxide.

The catalyst preferably comprises magnesium oxide. Magnesium oxide is basic, yet it is relatively stable in air. This is in contrast to calcium oxide, barium oxide and strontium oxide which react in air to form a carbonate which is not an effective catalyst for the present method. Hence, it is anticipated that calcium oxide, strontium oxide and barium oxide would be effective catalysts for the method of the present invention, but that appropriate precautions would need to be taken to ensure that the surface of those materials did not become contaminated prior to use. Magnesium oxide may be made by calcining magnesium hydroxide in a gas comprising oxygen, such as air. Calcining may comprising heating magnesium hydroxide in a gas comprising oxygen at one temperature for an extended period of time (for example, in excess of two hours) and then heating at a second, higher temperature (optionally in a gas comprising oxygen) for an extended period of time (for example, in excess of two hours). Magnesium oxide may be made by calcining magnesium hydroxide, then refluxing the product in a carrier liquid (such as water), then calcining the resulting product. This process produces a catalyst with a high surface area, which has proved to be desirable for the method of the present invention.

The term "metal" as used in the present application refers to elemental metals and metal ions.

The catalyst may have a BET surface area of at least 1 $m^2g^{-1}$, optionally at least 10 $m2g^{-1}$, optionally at least 20 $m^2g^{-1}$, typically at least 50 $m^2g^{-1}$, especially at least 80 $m^2g^{-1}$, more especially at least 100 $m^2g^{-1}$ and further more especially at least 120 $m^2g^{-1}$. The BET surface area was determined using the standard nitrogen adsorption technique.

The catalyst may be at a temperature of at least 200° C. when contacted with the polyol during the method of the present invention, optionally at no more than 350° C. and optionally at no more than 300° C. Whilst the use of a higher temperature generally increases conversion of the starting material, it has been discovered that the use of too high a temperature may, in certain circumstances, lead to an increased production of unwanted by-products. Optionally, the catalyst may be at a temperature of from 300° C. to 350° C. when contacted with polyol.

Contacting the polyol with the catalyst may take place in a flow reactor. It is anticipated that the method of the first aspect of the present invention may be performed using non-basic metal oxides. There is therefore provided in accordance with a second aspect of the present invention, a method of making one or more alcohols with a single hydroxy group, the method comprising contacting a polyol with a catalyst comprising a metal oxide. The catalyst may comprise a basic catalyst or an acidic catalyst. The method of the second aspect of the present invention may comprise those features described above in relation to the method of the first aspect of the present invention.

The method of the first aspect of the present invention may be used to generate products other than alcohols with a single hydroxy group. In accordance with a third aspect of the present invention, there is therefore provided a method of treating a polyol, said method comprising contacting said polyol with a basic catalyst in the presence of water at an ambient pressure of 5 atmospheres or less.

The ambient pressure when the polyol is contacted with the catalyst is typically 3 atmospheres or less, and optionally 2 atmospheres or less, and optionally from 1.0 to 1.5 atmospheres.

The method of the third aspect of the present invention may comprise those features described above in relation to the method of the first aspect of the present invention.

The catalyst used in the method of the second and third aspects of the present invention may have the characteristics and/or properties of the catalyst used in relation to the method of the first aspect of the present invention.

The invention will now be described by way of example only.

Catalysts for use in examples of methods of the present invention were manufactured as follows:

Catalyst A

Magnesium hydroxide (Aldrich) was heated at 10° C./min. to 450° C. and then calcined at 450° C. for 24 hours in air, then sieved using a 250-425 μm sieve, followed by refluxing with water for 3 hours to obtain a slurry. The slurry was dried at 110° C. for 24 hours and then heated to 600° C. at 10° C./min. and calcined at 600° C. for 3 hours under flowing nitrogen. The BET surface area of this catalyst was determined to be 144 $m^2g^{-1}$.

Catalyst B

Magnesium hydroxide (Aldrich) was heated at 10° C./min. to 450° C. and then calcined at 450° C. for 24 hours in air. The unsieved powder was then refluxed with water for 3 hours until a slurry was formed. The slurry was dried at 110° C. for 24 hours. The resulting material was then heated to 600° C. at 10° C./min ramp, and calcined for 3 hours at 600° C. under flowing nitrogen. The BET surface area of this catalyst was determined to be 107 $m^2g^{-1}$.

Catalyst C

Magnesium hydroxide (Aldrich) was heated at 10° C./min. to 450° C. and then calcined at 450° C. for 24 hours in air. The resulting material was then heated at 10° C./min. to 700° C., and then calcined at 700° C. for 24 hours. The BET surface area of this catalyst was determined to be 20 $m^2g^{-1}$.

Catalyst D

Magnesium hydroxide (Aldrich) was heated at 10° C./min. to 450° C. and then calcined at 450° C. in air and used directly. The BET surface area was determined to be 14 $m^2g^{-1}$.

Catalyst E

Catalyst A is doped with Li by placing Catalyst A in an aqueous solution of $LiNO_3$ (3 wt % of lithium in water) and heating at 70° C. until the excess water has evaporated to form a paste. The paste is then dried at 110° C. overnight, and the resulting product heated to 600° C. at 10° C./min, and then calcined at 600° C. for 3 h in air.

Catalyst F

Distilled water was added to a solution of manganese nitrate hydrate at 90° C., and stirred. The amount of water added was 10 mL of water/g of support. Magnesium hydroxide (Aldrich) was added to the solution, stirring continuously until a thick slurry was formed. The slurry was dried overnight. The product was heated in air at 10° C./min ramp to 800° C. and then calcined at 800° C. in air for 3 hours.

Catalyst G $Ca(OH)_2$ (Sigma Aldrich-99.99%) was heated at 10° C./min. to 450° C. and then calcined at 450° C. for 24 h in air. The resulting material was then refluxed with water for 3 hours. The slurry was dried at 110° C. overnight and then calcined at 600° C. for 3 h under nitrogen.

In catalysts H-J below, high surface area MgO catalysts A and B were used interchangeably since catalysts A and B were found to have very similar catalytic properties, particularly in relation to the catalysis of the synthesis of ethanol and methanol from glycerol.

Catalyst H

Catalyst A or B (75 wt %) was blended with Catalyst G (25 wt %) and thoroughly mixed.

Catalyst I

Catalyst A or B (50 wt %) was blended with Catalyst G (50 wt %) and thoroughly mixed.

Catalyst J

Catalyst A or B (25 wt %) was blended with Catalyst G (75 wt %) and thoroughly mixed.

Catalyst K $Sr(OH)_2$ octahydrate (Sigma Aldrich-95%) was heated at 10° C./min. to 450° C. and then calcined at 450° C. for 24 h in air. The resulting material was then refluxed with water for 3 hours. The slurry was dried at 110° C. overnight and then calcined at 600° C. for 3 hours under nitrogen.

Catalyst L

Dilute liquid ammonia was added to a 0.33M aqueous solution of lanthanum nitrate hexahydrate until a precipitate was formed. The precipitate was aged for 2 hours, filtered and washed several times with distilled water. The precipitate was dried overnight at 110° C. and activated by heating under nitrogen at a 10° C./min. ramp rate to 600° C., and then heating at 600° C. for 3 hours under nitrogen.
Catalyst M La(OH)$_3$ (Sigma Aldrich-99.9%) was heated at 10° C./min. to 450° C. and then calcined at 450° C. for 24 h in air. The resulting material was then refluxed with water for 3 hours. The slurry was dried at 110° C. overnight and then calcined at 600° C. for 3 hours under nitrogen.
Catalyst N Cerium octahydrate (Sigma Aldrich-95%) was heated at 10° C./min. to 450° C. and then calcined at 450° C. for 24 h in air. The resulting material was then refluxed with water for 3 hours. The slurry was dried at 110° C. overnight and then calcined at 600° C. for 3 hours under nitrogen.
Catalyst O 1M aqueous solution of magnesium nitrate hexahydrate was added dropwise to a 3M solution of anhydrous strontium nitrate with vigorous stirring at 70° C. Dilute liquid ammonia was then added until a precipitate was obtained. The solvent was allowed to evaporate at 70° C. and the precipitate was collected. The precipitate was heated at 10° C./min. ramp rate to 800° C. under nitrogen and then heated at 800° C. under nitrogen.

All of the above-mentioned catalysts were sieved using a 250-425 μm sieve prior to use.

The catalysts above were used in several examples of methods in accordance with the present invention as will now be described.

EXAMPLE 1

Synthesis of Methanol and Ethanol from Glycerol (propane-1,2,3-triol)

The reactions were carried out in a fixed bed flow reactor with an injection pump for feed injection, a pre-heater, a reactor (in the centre of which the catalyst was placed) and a product collection trap (at 0° C.). The reaction products were analysed and structures confirmed by GC, NMR, GC-MS and LC-MS (for the confirmation of formaldehyde). The carrier gas was helium or argon, the flow rate of which was kept constant at 100 ml/min. A solution of 0.5 wt % glycerol in water was passed over 0.25 g of heated catalyst at a rate of 1 ml/hour for a pre-determined time (usually three hours). In the present case, the catalyst was heated to a pre-determined temperature, in this case 250° C.

The conversion of glycerol for example is defined as:

$$100 - \left(100 \times \frac{C - \text{moles of glycerol collected}}{C - \text{moles of glycerol entering reactor}}\right)$$

Table 1 shows how the catalytic activity of the catalysts varied.

Catalysts A-E all showed catalytic activity towards the production of ethanol and methanol from glycerol. However, catalysts A and B showed far greater % conversion of glycerol than catalysts C and D, probably on account of the higher surface areas of catalysts A and B. A comparison between Methods 1A and 1F indicates that for this particular reaction, undesirable by-products are formed after the catalyst has been used for longer periods of time (in this case 5 hours).

TABLE 1

Conversion of glycerol and the selectivity (S) and yield (Y) (in C mole %) of the products recovered

| Method | Catalyst | Time for which catalyst used (hours) | MeOH S/Y | EtOH S/Y | acetol S/Y | acetaldehyde (or others) S/Y | Conversion (%) |
|---|---|---|---|---|---|---|---|
| 1A | A | 3 | 67/13.52 | 18/3.68 | 10/2 | 1/0.2 | 20 |
| 1B | B | 3 | 60/11.47 | 16/3.17 | 15/3 | 2/0.4 | 19 |
| 1C | C | 3 | 62/2.5 | 15/0.6 | 5/0.2 | — | 4 |
| 1D | D | 3 | 68/2.1 | 10/0.3 | 13/0.4 | — | 3 |
| 1E | E | 3 | 29/2.04 | — | 44/3.1 | 17/1.25 | 7 |
| 1F | A | 5 | 25/4.73 | 8/1.56 | 36/7 | 23/4.45 | 19 |
| 1G [1] | A | 3 | 64/10.95 | 18/3.2 | 10/1.8 | 1/0.3 | 17 |
| 1H [2] | A | 3 | 68/7.54 | 18/2 | 3/0.4 | 0.9/0.1 | 11 |

[1]—performed using C$^{13}$-glycerol and H$_2$O;
[2]—performed using C$^{13}$-glycerol and D$_2$O;
acetol is 1-hydroxy-2-propanone;
acetaldehyde is ethanal.
"Others" mentioned in Table 1 were one or more of ethane-1,2-diol, propane-1,2-diol and propenol.

Methods 1G and 1H were performed to investigate the source of the methanol and ethanol, and to identify the source of the hydrogen in methanol and ethanol. It was confirmed by NMR analysis that methanol and ethanol were derived from glycerol and water. In this connection, the methanol and ethanol produced in Method 1H contained C$^{13}$ and deuterium. The decrease in product yields in Method 1H relative to Methods 1A and 1G may be due to the isotopic effect of deuterium.

Attempts were made to reproduce Example 1 using calcium oxide as a catalyst. However, the calcium oxide demonstrated no catalytic activity. It is suspected that the calcium oxide had reacted with carbon dioxide in the air to form a shell of catalytically-inactive calcium carbonate around the calcium oxide. Given the positive results for magnesium oxide catalysts, it is expected that the more basic calcium oxide should give positive catalytic results if handled in such a way as to inhibit exposure of the calcium oxide to air or other reagents.

EXAMPLE 2

Synthesis of Methanol and Ethanol from propane-1,3-diol

The general methodology of Example 1 above was repeated using propane-1,3-diol instead of glycerol. The catalytic activity of the catalysts was investigated by varying the reaction time, the concentration of propane-1,3-diol, and catalyst temperature. Table 2 provides a summary of the results obtained.

TABLE 2

Conversion of propane-1,3-diol and the selectivity (S) and yield (Y) (in C mole %) of the products recovered over various catalysts

| Method | Catalyst | Time for which catalyst used (hours) | Concentration of 1,3-propanediol (wt %) | Catalyst temperature (°C.) | MeOH $S^1/Y^2$ | EtOH S/Y | acetaldehyde S/Y | Others S/Y | Conversion (%) |
|---|---|---|---|---|---|---|---|---|---|
| 2A | A | 3 | 0.5 | 220 | 27/20 | 24/18.4 | 37/28 | 6/5.2 | 75 |
| 2B | A | 3 | 0.5 | 250 | 27/27 | 21/21 | 38/38 | 7/7.3 | 100 |
| 2C | A | 3 | 0.5 | 290 | 31/31 | 18/18.8 | 43/43.4 | 5/5.3 | 100 |
| 2D | A | 3 | 0.5 | 330 | 27/27 | 18/18 | 44/44 | 3.6/3.6 | 100 |
| 2E | A | 6 | 0.5 | 290 | 29/29 | 18/18.5 | 35/35 | 8/8.3 | 100 |
| 2F | E | 3 | 0.5 | 290 | 31/31 | 13/13.92 | 43/43 | 10/10.5 | 100 |
| 2G | A | 3 | 3 | 250 | 19/17.6 | 17/16 | 24/22 | 24/22 | 90 |
| 2H | A | 3 | 3 | 290 | 23/22.4 | 20/19.5 | 28/27.9 | 17/17 | 97 |
| 2I | A | 3 | 3 | 330 | 25/25 | 19/19 | 35/35 | 15/15 | 100 |
| 2J | A | 3 | 3 | 370 | 25/25 | 18/18 | 39/39 | 11/11 | 100 |
| 2K | E | 3 | 3 | 290 | 22/14.4 | 18/11.5 | 31/20.1 | 22/14.3 | 63 |
| 2L | A (0.5 g) | 3 | 10 | 330 | 26/26 | 18/18.4 | 31/31 | 19/19 | 100 |

The data from Table 2 indicate that catalysts A and E are effective in catalysing the generation of methanol and ethanol from propane-1,3-diol. Conversion of the diol was very high, as indicated in the table. The table indicates that conversion is sensitive to temperature; if the catalyst is at too low a temperature, then conversion is less than 100%. The data from Table 2 also indicate that this reaction may be catalysed over a wide concentration range of polyol.

"Others" in Table 2 includes propenal and propanal, and, at higher temperatures, propan-1-ol and prop-2-en-1-ol.

EXAMPLE 3

Synthesis of Methanol and Ethanol from Ethylene Glycol (1,2-ethanediol)

The general methodology of Example 1 above was repeated using ethylene glycol instead of glycerol. The temperature of the catalyst was 290° C. The effect of concentration of ethylene glycol and flow rate of the solution of ethylene glycol was investigated.

TABLE 3

Conversion of 1,2-ethanediol and the selectivity (S) and yield (Y) (in C mole %) of the products recovered over various catalysts

| Method | Catalyst | Concentration of ethylene glycol (wt %) | Flow rate (ml/hour) | Time for which catalyst used (hours) | MeOH S/Y | EtOH S/Y | Acetaldehyde S/Y | Conversion (%) |
|---|---|---|---|---|---|---|---|---|
| 3A | A | 0.5 | 1 | 3 | 20/4.5 | 68/15 | 1/0.3 | 22 |
| 3B | A | 0.5 | 1 | 6 | 18/3.7 | 59/11.9 | 4.5/0.9 | 20 |
| 3C | A | 3 | 0.5 | 3 | 21/3 | 50/7.1 | 13/1.9 | 14 |

Table 3 indicates that catalyst A is an effective catalyst for the production of methanol and ethanol from ethylene glycol. However, the % conversion of ethylene glycol is a lot lower than for propane-1,3-diol. Furthermore, whilst the selectivity (and to a lesser extent the yield) for methanol seems to be relatively insensitive to reaction time and the concentration of the ethylene glycol, the yield and selectivity for ethanol seem to be sensitive to both the time for which the catalyst is used and the concentration of ethylene glycol.

EXAMPLE 4

Synthesis of Methanol and Ethanol from butane-1,4-diol

The general methodology of Example 1 above was repeated using butane-1,4-diol instead of glycerol. The effect of catalyst temperature on catalytic activity was investigated.

TABLE 4

Conversion of butane-1,4-diol and the yield (Y) (in C mole %) of the products recovered over various catalysts

| Method | Catalyst | Catalyst temperature (° C.) | MeOH Y | EtOH Y | Acetaldehyde Y | Others Y | Conversion (%) |
|---|---|---|---|---|---|---|---|
| 4A | A | 250 | 2 | 5 | 0.3 | 53.7 | 84 |
| 4B | A | 290 | 2.2 | 5.2 | 0.5 | 77.9 | 87 |
| 4C | A | 340 | 3 | 8.6 | 0.1 | 55.3 | 82 |
| 4D | A | 390 | 4.3 | 12 | 1.1 | 68.6 | 97 |

Catalyst A acts as an effective catalyst in the conversion of butane-1,4-diol. However, the yield of both methanol and ethanol are low compared to other polyols.

"Others" in Table 4 includes prop-2-en-1-ol and propan-1-ol.

EXAMPLE 5

Synthesis of Methanol and Ethanol from Glycerol using MgO Catalyst (Catalyst A or B)—the Effect of Glycerol Concentration at a Catalyst Temperature of 250° C.

The general methodology of Example 1 above was repeated using different concentrations of glycerol at 250° C.

TABLE 5 conversion of glycerol and product selectivities as a function of concentration of glycerol at 250° C.

| Glycerol conc. | Conv. | Product selectivities (mol %) | | | | | |
|---|---|---|---|---|---|---|---|
| (wt %) | (mol %) | MeOH | EtOH | Acetol | Ethanal | Acrolein | EG* |
| 0.5[1] | 20 | 65 | 20 | 11 | 2 | 0 | 0 |
| 10[2] | 5 | 33 | 0 | 32 | 7 | 11 | 17 |
| 10[2] | 6 | 31 | 0 | 34 | 8 | 10 | 15 |

Catalyst
[1]0.25 g catalyst,
[2]0.5 g catalyst,
*ethylene glycol.

The data from Table 5 indicate that whilst the % conversion of glycerol and selectivity for methanol and ethanol decrease when the glycerol concentration is increased from 0.5 wt % to 10 wt %, there is still an appreciable amount of methanol produced at 10 wt % glycerol. It is notable that selectivity for ethanol decreases dramatically when the feed concentration of glycerol is increased from 0.5 wt % to 10 wt %.

EXAMPLE 6

Synthesis of Methanol and Ethanol from Glycerol using MgO Catalyst (Catalyst A or B)—the Effect of Glycerol Concentration at a Catalyst Temperature of 300° C.

The general methodology of Example 1 above was repeated using different concentrations of glycerol at 300° C.

The data from Table 6 indicate that the % conversion of glycerol and selectivity for methanol and ethanol change very little when the glycerol concentration is increased from 10 wt % to 30 wt %.

TABLE 6 conversion of glycerol and product selectivities as a function of concentration of glycerol at 300° C.

| Glycerol conc. | Conv. | Product selectivities (mol %) | | | | | |
|---|---|---|---|---|---|---|---|
| (wt %) | (mol %) | MeOH | EtOH | Acetol | Ethanal | Acrolein | EG |
| 10[1] | 25 | 45 | 2 | 25 | 13 | 9 | 4 |
| 20[2] | 20 | 40 | 1 | 30 | 11 | 7 | 12 |
| 30[3] | 25 | 37 | 1 | 34 | 14 | 9 | 4 |

[1]0.5 g of catalyst,
[2]0.75 g of catalyst,
[3]1 g of catalst

EXAMPLE 7

Synthesis of Methanol and Ethanol from Glycerol using MgO Catalyst (Catalyst A or B)—the Effect of Catalyst Temperature The general methodology of Example 1 above was repeated using different catalyst temperatures, but with a glycerol concentration of 10 wt % and 0.5 g of catalyst.

TABLE 7 conversion of glycerol and product selectivities as
a function of catalyst temperature

| Temperature (°C.) | Conv. (mol %) | Product selectivities (mol %) | | | | |
|---|---|---|---|---|---|---|---|
| | | MeOH | EtOH | Acetol | Ethanal | Acrolein | EG |
| 250 | 5 | 33 | 0 | 32 | 7 | 11 | 17 |
| 280 | 18 | 41 | 2 | 31 | 11 | 9 | 4 |
| 300 | 25 | 45 | 2 | 25 | 13 | 9 | 4 |

The data from Table 7 indicate that the % conversion of glycerol and selectivity for methanol increases when the temperature of the catalyst is increased from 250° C. to 300° C.

EXAMPLE 8

Synthesis of Methanol and Ethanol from Glycerol using MgO Catalyst—the Effect of 1 wt % Manganese The general methodology of Example 1 above was repeated using different catalyst temperatures and a different catalyst, but with a glycerol concentration of 10 wt %, 0.5 g of catalyst.

TABLE 8 conversion of glycerol and product selectivities as
a function of temperature and as a function of the presence or
absence of 1 wt % manganese

| Catalyst | Temperature (°C.) | Conv. (mol %) | Product selectivities (mol %) | | | | | |
|---|---|---|---|---|---|---|---|---|
| | | | MeOH | EtOH | Acetol | Ethanal | Acrolein | EG |
| A or B | 280 | 18 | 41 | 2 | 31 | 11 | 9 | 4 |
| F | 280 | 7 | 30 | 1 | 15 | 17 | 10 | 18 |
| A or B | 300 | 25 | 45 | 2 | 25 | 13 | 9 | 4 |
| F | 300 | 10 | 34 | 2 | 13 | 18 | 10 | 22 |
| A or B | 320 | 23 | 41 | 2 | 26 | 14 | 8 | 8 |
| F | 320 | 13 | 41 | 2 | 17 | 19 | 12 | 4 |

The data from Table 8 indicate that the % conversion of glycerol is lower at the selected catalyst temperatures when manganese is incorporated into the MgO catalyst. The data indicated that for the catalyst incorporating the manganese, the % conversion increases from 280° C. to 320° C., but for the MgO on its own, the % conversion is better at 300° C. than at lower and higher temperatures.

EXAMPLE 9

Synthesis of Methanol and Ethanol from Glycerol using MgO, CaO or a Mixture of the Two as a Catalyst, as a Function of Temperature The general methodology of Example 1 above was repeated using either magnesium oxide, calcium oxide or a mixture of the two as catalyst. The method used 10 wt % glycerol and 0.5 g catalyst.

In the examples below, $g_{MeOH} kg_{cat.}^{-1} h^{-1}$ refers to the mass of methanol made per kg of catalyst per hour. The data of Table 9 indicate that conversion increases with increasing temperature. The data also indicate that catalysts containing CaO at higher temperatures (such as 320° C. and 340° C.) give a higher conversion than MgO alone, whilst MgO alone gives higher conversion at lower temperatures (250° C. and 280° C.) Selectivity for methanol appears to be better for catalysts containing CaO than for MgO alone. The data also illustrate that large amounts of methanol can be made, even at high temperatures, especially when using catalysts containing CaO.

TABLE 9 conversion of glycerol and product selectivities as a function of temp. and catalyst

| | Temperature (°C.) | | | | | | | | | | | | | | | | | |
|---|---|---|---|---|---|---|---|---|---|---|---|---|---|---|---|---|---|---|
| | 250 | | 280 | | | | 300 | | | | | 320 | | | | 340 | | |
| | Catalysts | | | | | | | | | | | | | | | | | |
| | A/B | G | A/B | H | I | J | G | A/B | H | I | J | G | A/B | H | I | J | G | I | G |
| Conversion (mol. %) | 6 | 3 | 17 | 14 | 15 | 13 | 10 | 24 | 20 | 21 | 24 | 17 | 27 | 35 | 38 | 40 | 35 | 45 | 39 |

TABLE 9-continued conversion of glycerol and product selectivities as a function of temp. and catalyst

| | Temperature (° C.) | | | | | | | | | | | | | | | | | | |
|---|---|---|---|---|---|---|---|---|---|---|---|---|---|---|---|---|---|---|---|
| | 250 | | 280 | | | | 300 | | | | | 320 | | | | | 340 | | |
| | | | | | | | Catalysts | | | | | | | | | | | | |
| | A/B | G | A/B | H | I | J | G | A/B | H | I | J | G | A/B | H | I | J | G | I | G |
| Selectivities (mol. %) | | | | | | | | | | | | | | | | | | | |
| MeOH | 31 | 72 | 41 | 50 | 63 | 64 | 65 | 45 | 51 | 62 | 60 | 66 | 41 | 53 | 62 | 64 | 62 | 58 | 51 |
| EtOH | 0 | 0 | 2 | 2 | 2 | 2 | 1 | 2 | 2 | 2 | 2 | 2 | 2 | 4 | 5 | 9 | 7 | 8 | 14 |
| Acetol | 34 | 6 | 31 | 15 | 10 | 17 | 13 | 22 | 15 | 11 | 17 | 13 | 26 | 14 | 11 | 6 | 12 | 7 | 2 |
| Ethanal | 8 | 10 | 11 | 12 | 7 | 8 | 9 | 16 | 11 | 9 | 8 | 9 | 14 | 12 | 11 | 11 | 13 | 13 | 13 |
| Acrolein | 10 | 5 | 9 | 11 | 5 | 5 | 3 | 9 | 10 | 6 | 4 | 2 | 8 | 9 | 4 | 2 | 1 | 4 | 1 |
| Ethylene glycol | 15 | 5 | 4 | 7 | 5 | 3 | 7 | 4 | 7 | 8 | 5 | 6 | 8 | 7 | 3 | 3 | 2 | 1 | 1 |
| Propanal | 0 | 1 | 1 | 1 | 1 | 1 | 1 | 1 | 1 | 1 | 1 | 1 | 1 | 1 | 1 | 1 | 1 | 2 | 2 |
| Allyl alcohol | 0 | 0 | 1 | 1 | 1 | 1 | 0 | 1 | 1 | 1 | 1 | 0 | 1 | 1 | 1 | 0 | 0 | 1 | 0 |
| Acetone | 0 | 0 | 0 | 1 | 1 | 1 | 0 | 1 | 0 | 1 | 1 | 0 | 0 | 1 | 2 | 3 | 3 | 6 | 8 |
| $g_{MeOH}$ $kg_{cat.}^{-1}$ $h^{-1}$ | 1 | 1.7 | 4.7 | 4.5 | 6.1 | 6.4 | 4.1 | 7.1 | 7.5 | 8.1 | 10.1 | 7.5 | 7.3 | 13.4 | 14.7 | 16.5 | 14.3 | 16.9 | 12.8 |

EXAMPLE 10

Synthesis of Methanol and Ethanol from Glycerol using Various Catalysts as a Function of Temperature The general methodology of Example 1 above was repeated using different catalyst temperatures and different catalysts, but with a glycerol concentration of 10 wt %, 0.5 g of catalyst. The results are shown in Tables 10 and 11 below.

The data from Tables 10 and 11 demonstrate the effect of different catalysts at different temperatures on the production of methanol and other products. For example, $Ce_2O_3$ provides a high conversion at high temperatures, and has a high selectivity for methanol at those high temperatures.

Whilst not wishing to be bound by theory, studies have been undertaken using glycerol to determine a likely reaction mechanism. Investigations using $D_2O$ indicate that the water is acting as a hydrogen source for the formation of methanol. The products obtained from the reaction suggest that there is catalyst-assisted C—C cracking of the glycerol to form acrolein which may then be reduced to form propanal and allyl alcohol, acetol which may be reduced to form acetone, methanol, and an ethylene glycol radical which forms acetaldehyde and ethylene glycol, the ethylene glycol being cleavable to form ethanol.

TABLE 10

| | 300° C. | | | | 320° C. | | | | 340° C. | | |
|---|---|---|---|---|---|---|---|---|---|---|---|
| Components | A/B | G | K | L | A/B | G | K | L | A/B | K | L |
| MeOH % selectivity | 45 | 66 | 61 | 30 | 41 | 62 | 55 | 31 | 51 | 55 | 32 |
| EtOH % selectivity | 2 | 2 | 3 | 2 | 2 | 7 | 8 | 2 | 14 | 3 | 2 |
| Acetol % selectivity | 25 | 13 | 18 | 18 | 26 | 12 | 13 | 19 | 2 | 9 | 15 |
| Ethanal % selectivity | 13 | 9 | 9 | 28 | 14 | 13 | 12 | 26 | 13 | 12 | 27 |
| Acrolein % selectivity | 9 | 2 | 1 | 6 | 8 | 1 | 0 | 8 | 1 | 1 | 5 |
| EG % selectivity | 4 | 6 | 6 | 3 | 8 | 2 | 3 | 2 | 1 | 1 | 1 |
| Propanal % selectivity | 1 | 1 | 1 | 1 | 1 | 1 | 1 | 1 | 2 | 1 | 2 |
| Allyl alcohol % selectivity I | 1 | 0 | 0 | 0 | 1 | 0 | 0 | 0 | 0 | 0 | 0 |
| Acetone/unknown % selectivity | 0 | 0 | 3 | 3/8 | 0 | 3 | 5 | 4/6 | 8 | 12 | 9/7 |
| Conversion % | 25 | 17 | 15 | 15 | 27 | 35 | 20 | 20 | 37 | 28 | 32 |
| $g_{MeOH}$ $kg_{cat.}^{-1}$ $h^{-1}$ | 7.1 | 7.52 | 5.8 | 3.8 | 7.3 | 14.35 | 7.4 | 4.79 | 12.87 | 10.3 | 7.74 |

TABLE 11

| | 300° C. | | | 320° C. | | | 340° C. | | |
|---|---|---|---|---|---|---|---|---|---|
| Components | M | N | O | M | N | O | M | N | O |
| MeOH % selectivity | 33 | 39 | 55 | 33 | 41 | 43 | 35 | 50 | 47 |
| EtOH % selectivity | 2 | 2 | 3 | 2 | 3 | 12 | 2 | 5 | 14 |
| Acetol % selectivity | 20 | 3 | 19 | 7 | 2 | 15 | 8 | 0 | 7 |
| Ethanal % selectivity | 31 | 21 | 9 | 28 | 18 | 8 | 29 | 13 | 14 |
| Acrolein % selectivity | 8 | 2 | 2 | 9 | 1 | 3 | 6 | 0 | 2 |
| EG % selectivity | 2 | 1 | 1 | 2 | 4 | 2 | 3 | 3 | 2 |
| Propanal % selectivity | 1 | 4 | 1 | 2 | 5 | 1 | 3 | 3 | 2 |
| Allyl alcohol % selectivity | 0 | 2 | 1 | 5 | 1 | 2 | 1 | 2 | 1 |

TABLE 11-continued

| | 300° C. | | | 320° C. | | | 340° C. | | |
|---|---|---|---|---|---|---|---|---|---|
| Components | M | N | O | M | N | O | M | N | O |
| Acetone/unknown % selectivity | 3 | 7/17 | 3/7 | 4/9 | 9/13 | 2/12 | 5/10 | 14/10 | 7/4 |
| Conversion % | 12 | 25 | 5 | 16 | 40 | 13 | 20 | 50 | 22 |
| $g_{MeOH}\,kg_{cat.}^{-1}\,h^{-1}$ | 3.1 | 7.5 | 2 | 4.2 | 10.3 | 4 | 5.1 | 16.8 | 8.4 |

The example methods above use water. It is anticipated that alternative liquids may be used.

The example methods above use magnesium oxide as a catalyst. Those skilled in the art will realise that alternative basic catalysts may be used. For example, calcium oxide may be used if surface of the calcium oxide is kept "clean" i.e. free of contaminants, such as calcium carbonate. This may be achieved by keeping calcium oxide in an inert atmosphere prior to use. Alternatively, the oxides of lanthanides may be used.

The methods above concentrate on the formation of methanol and ethanol. The method of the present invention may be used to make other mono-ols (alcohols with a single hydroxy group).

The example methods above use a flow reactor. Those skilled in the art will realise that other reactors and methods may be used.

Where, in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable; advantageous, convenient or the like are optional and do not limit the scope of the independent claims.

The invention claimed is:

1. A method of making one or more alcohols with a single hydroxy group, the method comprising:
    contacting a polyol with a basic catalyst comprising one or more alkaline earth metals in the presence of water, wherein the ambient pressure when the polyol is contacted with the basic catalyst is 5 atmospheres or lower, and the weight of the polyol is from 0.003 to 0.1 times the weight of the water.

2. The method according to claim 1, comprising a method of making one or both of methanol and ethanol.

3. The method according to claim 1, wherein the polyol is mixed with the water.

4. The method according to claim 1, wherein the ambient pressure when the polyol is contacted with the basic catalyst is 2 atmospheres or less.

5. The method according to claim 1, wherein the basic catalyst is at a temperature of from 200° C. to 350° C. when contacted with the polyol.

6. The method according to claim 5, wherein the basic catalyst is at a temperature of from 300° C. to 350° C. when contacted with the polyol.

7. The method according to claim 1, wherein the basic catalyst comprises one or more oxides of one or more alkaline earth metal.

8. The method according to claim 7, wherein the basic catalyst comprises one or more of magnesium oxide, calcium oxide, strontium oxide and barium oxide.

9. The method according to claim 1, wherein the polyol may comprise a polyhydroxyalkane.

10. The method according to claim 9, wherein the polyol comprises propane-1,2-diol, propane-1,3-diol, propane-1,2,3-triol or butane-1,2-diol.

11. The method according to claim 1, wherein the polyol comprises a sugar.

12. The method according to claim 1, wherein the basic catalyst has a BET surface area of at least 50 m²g⁻¹.

13. A method of making methanol and/or ethanol from a polyol comprising propane-1,2-diol, propane-1,3-diol, propane-1,2,3-triol or butane-1,2-diol, the method comprising:
    contacting the polyol with a basic catalyst comprising MgO and CaO in the presence of water,
    wherein the ambient pressure when the polyol is contacted with the basic catalyst is 5 atmospheres or lower,
    the basic catalyst being at a temperature of from 200° C. to 350° C. when the polyol is contacted with the basic catalyst, and
    the weight of the polyol is from 0.003 to 0.1 times the weight of the water.

14. A method of making one or more alcohols with a single hydroxy group, the method comprising contacting a polyol with a catalyst in the presence of water, the catalyst consisting essentially of:
    (i) one or more oxides of one or more alkaline earth metals, or
    (ii) one or more oxides of one or more lanthanides, or
    (iii) one or more oxides of one or more alkaline earth metals and one or more oxides of one or more lanthanides; and
    the ambient pressure when the polyol is contacted with the catalyst being 5 atmospheres or lower.

15. The method according to claim 14, the catalyst comprising one or more oxides of cerium.

16. The method according to claim 14, the catalyst comprising magnesium oxide.

17. The method according to claim 16, the catalyst further comprising calcium oxide.

18. The method according to claim 14, the weight of the polyol is from 0.001 to 0.5 times the weight of the water.

19. The method according to claim 1, the catalyst consisting essentially of:
    (i) one or more oxides of one or more alkaline earth metals, or
    (ii) one or more oxides of one or more lanthanides, or
    (iii) one or more oxides of one or more alkaline earth metals and one or more oxides of one or more lanthanides.

* * * * *